United States Patent
Mash

(10) Patent No.: US 7,220,737 B1
(45) Date of Patent: May 22, 2007

(54) NORIBOGAINE IN THE TREATMENT OF PAIN AND DRUG ADDICTION

(75) Inventor: Deborah C. Mash, North Bay Village, FL (US)

(73) Assignee: Novoneuron, Inc, Miami, FL (US)

( * ) Notice: Subject to any disclaimer, the term of this patent is extended or adjusted under 35 U.S.C. 154(b) by 0 days.

(21) Appl. No.: 09/486,613

(22) PCT Filed: Sep. 3, 1998

(86) PCT No.: PCT/US98/18284

§ 371 (c)(1),
(2), (4) Date: Feb. 29, 2000

(87) PCT Pub. No.: WO99/12744

PCT Pub. Date: Mar. 18, 1999

Related U.S. Application Data

(60) Provisional application No. 60/057,921, filed on Sep. 4, 1997.

(51) Int. Cl.
*A01N 43/00* (2006.01)
*A61K 31/55* (2006.01)
*A61K 31/00* (2006.01)
*A61K 31/397* (2006.01)
*A61K 31/407* (2006.01)

(52) U.S. Cl. .................... 514/214.03; 514/214.01; 514/214.02; 514/210.21; 514/210.2; 514/210.1; 514/210.05

(58) Field of Classification Search ........... 514/211.04, 514/211.01, 211.02, 415, 410, 422, 210.21, 514/210.2, 210.19, 210.05, 214.02, 214.03, 514/214.01, 210.1, 210.02, 210.03
See application file for complete search history.

(56) References Cited

U.S. PATENT DOCUMENTS

| | | | |
|---|---|---|---|
| 3,516,989 A | 6/1970 | Sallay | |
| 3,557,126 A | 1/1971 | Sallay | |
| 3,574,220 A | 4/1971 | Sallay | |
| 3,639,408 A | 2/1972 | Nagata et al. | |
| 3,715,361 A | 2/1973 | Epstein et al. | |
| 3,875,011 A | 4/1975 | Rubenstein et al. | |
| 4,272,541 A | 6/1981 | Kotick et al. | |
| 4,375,414 A | 3/1983 | Strahilevitz | |
| 4,444,758 A | 4/1984 | Scherschlicht et al. | |
| 4,462,941 A | 7/1984 | Lee et al. | |
| 4,464,378 A * | 8/1984 | Hussain | 424/260 |
| 4,499,096 A | 2/1985 | Lotsof | |
| 4,587,243 A | 5/1986 | Lotsof | |
| 4,604,365 A | 8/1986 | O'Neill et al. | |
| 4,620,977 A | 11/1986 | Strahilevitz | |
| 4,661,492 A | 4/1987 | Lewis et al. | |
| 4,857,523 A | 8/1989 | Lotsof | |
| 5,026,697 A | 6/1991 | Lotsof | |
| 5,075,341 A | 12/1991 | Mendelson et al. | |
| 5,149,538 A | 9/1992 | Granger et al. | |
| 5,152,994 A | 10/1992 | Lotsof | |
| 5,283,247 A | 2/1994 | Dwivedi et al. | |
| 5,290,784 A | 3/1994 | Qu et al. | |
| 5,316,759 A | 5/1994 | Rose et al. | |
| 5,426,112 A | 6/1995 | Zagon et al. | |
| 5,552,406 A | 9/1996 | Mendelson et al. | |
| 5,574,052 A | 11/1996 | Rose et al. | |
| 5,580,876 A * | 12/1996 | Crain et al. | 514/282 |
| 5,591,738 A | 1/1997 | Lotsof | |
| 5,618,555 A | 4/1997 | Tokuda et al. | |
| 5,703,101 A | 12/1997 | Rose et al. | |
| 5,726,190 A | 3/1998 | Rose et al. | |
| 5,760,044 A * | 6/1998 | Archer | 514/282 |
| 5,861,422 A | 1/1999 | Rose et al. | |
| 5,925,634 A * | 7/1999 | Olney | 514/214.03 |
| 5,935,975 A | 8/1999 | Rose et al. | |
| 6,348,456 B1 * | 2/2002 | Mash et al. | 514/214.03 |

FOREIGN PATENT DOCUMENTS

| | | |
|---|---|---|
| DE | 2217132 | 10/1972 |
| GB | 841697 | 7/1960 |
| GB | 924042 | 4/1963 |
| GB | 1256914 | 12/1971 |
| GB | 2271059 | 4/1994 |
| JP | 4221315 | 8/1992 |
| WO | WO 91/18609 | 12/1991 |
| WO | WO 93/20825 | 10/1993 |
| WO | WO 93/25217 | 12/1993 |
| WO | WO 94/06426 | 3/1994 |
| WO | WO 94/14490 | 7/1994 |
| WO | WO 96/03127 | 2/1996 |
| WO | WO9603127 | 2/1996 |

OTHER PUBLICATIONS

Hardman et al. "Goodman & Gilman's The Parmacological Basis of Therapeutics" (9th ed, 1996) p. 51 and 57-58.*

(Continued)

*Primary Examiner*—Sreeni Padmanabhan
*Assistant Examiner*—Abigail M. Cotton
(74) *Attorney, Agent, or Firm*—Henry D. Coleman; R. Neil Sudol; William J. Sapone

(57) ABSTRACT

The present invention is directed to methods of treating patients for pain by administering noribogaine. Noribogaine may also be used to treat patients for the symptoms associated with withdrawal from drug dependency. In the latter case, the noribogaine treatment should be supplemented with the administration of an opioid antagonist such as naloxone.

9 Claims, 1 Drawing Sheet

OTHER PUBLICATIONS

Mash et al, Properties of Ibogaine and its Principle Metabolite (12-hydroxyibogamine) at the MK-801 binding site of the NMDA receptor complex, 1995, Neuroscience Letters, 192, 53-56.*

Pablo et al, Noribogaine Stimulates Naloxone-Sensitive[35S]GTPgammaS Binding, 1998, NeuroReport, 9, pp. 109-114. (Website Publication Date of Dec. 20, 1997.).*

Mark J. Millan, k-Opioid Receptors and Analgesia, 1990, Trendes in Pharmacologicla Sciences, 11, pp. 70-76.*

Pablo, John P. and Mash, Deborah C. "Noribogaine Stimulates Naloxane-Sesitive [$^{35}$S]GTPγS Binding", *NeuroReport*, 9: pp. 109-114, 1998.

Bagal et al. "Modulation of Morphine-Induced Antinociception by Ibogaine and Noribogaine", *Brain Research*, 741: pp. 258-262, 1996.

Bundgaard, Hans. "Design of Prodrugs: Bioreversible Derivatives for Various Functional Groups and Chemical Entities", *Design of Prodrugs*, (New York, Elsevier Science Publishers, 1985).

Schuckit, M. A. et al. "Opioid Drug Use", in Isselbacher, K.J. et al., *Harrisoné Principles of Internal Medicine* (New York, McGraw-Hill, 1994) pp. 2425-2429.

Holbrook, J. H. "Nicotine Addiction", in Isselbacher K.J. et al., *Harrison's Principles of Internal Medicine*, (New York, McGraw-Hill, 1994) pp. 2433-2437.

Jaffe, J. H. "Drug Addiction and Drug Abuse", in Gilman A.G. et al., *Goodman and Gilman's The Pharmacological Basis of Therapeutics*, (New York, Pergamon Press, 1990) pp. 520-523 and pp. 559-568.

Stella, V. "Pro-drugs as Novel Drug Delivery Systems", Higuchi, T. et al., ed. (American Chemical Society, Washington), pp. 1-49 (1975).

Maisonneuve, I. M. et al. "Interactions of Ibogaine and D-Amphetamine: in Vivo Microdialysis and Motor Behavior in Rats", *Brain Research*, 579: pp. 87-92, 1992.

Benet, L. Z. et al. "Pharmacokinetics: The Dynamics of Drug Absorption, Distribution, and Elimination", in Gilman, A.G. et al., *Goodman and Gilman's The Pharmacological Basics of Therapeutics*, (New York, Pergamon Press, 1990), pp. 13-16.

Bartlett, M. F. et al. "The Alkaloids of *Tabernanthe iboga*. Part IV.[1] The Structures of Ibogamine, Ibogaine, Tabernanthine and Voacangine", *J. Am. Chem. Soc.*, 80: pp. 126-136, 1958.

Kornetsky, Conan. "Pharmacology Drugs Affecting Behavior", (New York, John Wiley & Sons, 1976), pp. 186.

Deecher, D. C. et al. "Mechanisms of Action of Ibogaine and Harmaline Congeners Based on Radioligand Binding Studies", *Brain Research*, 571(2): pp. 242-247, 1992.

Sinkula, A. A. et al. "Rationale for Design of Biologically Reversible Drug Derivatives: Prodrugs", *Journal of Pharmaceutical Sciences*, 64: pp. 181-210, Feb. 1975.

Zetler, G. et al. "Pharmacokinetic in the Rat of the Hallucinogenic Alkaloids Harmine and Harmaline", *Naunyn-Schmiedeberg's Arch. Pharmacol.*, 285: pp. 273-292, 1974.

Glick, S. D. et al. "Effects of *iboga* Alkaloids on Morphine and Cocaine Self-Administration in Rats: Relationship to Tremorigenic Effects and to Effects on Dopamine Release in Nucleus Accumbens and Striatum", *Brain Research*, 657: pp. 14-22, 1994.

Cappendijk, Susanne et al. "The Inhibitory Effect of Norharman on Morphine Withdrawal Syndrome in Rats: Comparisons with Ibogaine", *Behavioural Brain Research*, Faculty of Medicine and Health Sciences, Eramus University Rotterdam, 3000 Dr., Rotterdam, The Netherlands, Aug. 5, 1994, pp. 1-3.

Gunn. J. A. "Relations Between Chemical Constitution, Pharmacological Actions, and Therapeutic Uses, in the Harmine Group of Alkaloids", *The Pharmacological Laboratory, University of Oxford*, Mar. 14, 1935, pp. 379-383, pp. 395-396.

Slotkin, Theodore A. and DiStefano, Victor. "A Model of Harmine Metabolism in the Rat", *The Journal of Pharmacology and Experimental Therapeutics*, Department of Pharmacology, University of Rochester, Rochester, New York, The Williams & Wilkins Co., 174(3): pp. 456-462, 1970.

Ho, Beng T. et al. "Metabolish of Harmaline in Rats", *Biochemical Pharmacology*, 20: pp. 1313-1319, 1971.

Slotkin, Theodore A. et al. "Blood Levels and Urinary Excretion of Harmine and Its Metabolites in Man and Rats", *The Journal of Pharmacology and Experimental Therapeutics*, 173(1): pp. 26-30, 1970.

Slotkin, Theodore and DiStefano, Victor. "Urinary Metabolites of Harmine in the Rat and Their Inhibition of Monoamine Oxidase", *Biochemical Pharmacology*, 19: pp. 125-131, 1970.

Glick, S. D. et al. "Effects of Aftereffects of Ibogaine on Morphine Self-Administration in Rats", *European Journal of Pharmacology*, 195(3): abstract only, 1991.

Dzoljic, E. D. et al. "Effect of Ibogaine on Naloxone-Precipitated Withdrawal Syndrome in Chronic Morphine-Dependent Rats", *Archives Internationales de Pharmacodynamie et de Therapie*, 294: abstract only, 1988.

Schechter, M. D. et al. "Comparison of the Behavioral Effects of Ibogaine from Three Sources: Mediation of Discriminative Activity", *European Jornal of Pharmacology*, 249(1): abstract only, 1993.

Popik, P. et al. "The Putative Anti-Addictive Drug Ibogaine is a Competitive Inhibitor of ( SUP 3 H) Binding to the NMDA Receptor Complex", *Psychopharmacologia*, 114(4): abstract only, 1994.

Harsing, L.G. Jr. et al. "Evidence that Ibogaine Releases Dopamine from the Cytoplasmic Pool in Isloated Mouse Striatum", *Journal of Neural Transmission General Section*, 96(3): abstract only, 1994.

Cappendijk, Susanne L. T. and Dzoljic, Michailo R. "Inhibitory Effects of Ibogaine on Cocaine Self-Administration in Rats", *Eur. J. Pharmacol.*, 241 (2-3): abstract only, 1993.

Sershen, Hery et al. "Ibogaine Antagonizes Cocaine-Induced Locomotor Stimulation in Mice", *Life Sci.*, 50(15): abstract only, 1992.

Sershen, Henry et al. "Ibogaine Reduces Amphetamine-Induced Locomotor Stimulation in C57BL/6By Mice, but Stimulates Locomotor Activity in Rats", *Life Sci.*, 51(13): abstract only, 1992.

Glick, S. D. et al. Local Effects of Ibogaine on Extracellular Levels of Dopamine and Its Metabolites in Nucleus Accumbens and Striatum: Interactions with D-Amphetamine, *Brain Research*, 628: abstract, 1993.

Maisonneuve, I. M. et al. "Acute and Prolonged Effects of Ibogaine on Brain Dopamine Metabolism and Morphine-Induced Locomotor Activity in Rats", *Brain Research*, 575(1): abstract only, 1992.

Maisonneuve, I. M. et al. "Interactions Between Ibogaine, a Potential Anti-Addictive Agent, and Morphine: an in Vivo Microdialysis Study", *Eur. J. Pharmacol.*, 199(1): abstract only, 1991.

Fonne-Pfister, Raymonde and Meyer, Urs A. "Xenobiotic and Endobiotic Inhibitors of Cytochrome P-450dbl Function, the Target of the Debrisoquine / Sparteine Type Polymorphism", *Biochem. Pharmacol.*, 37(20): abstract only, 1988.

Jane, I. et al. "High-Performance Liquid Chromatographic Analysis of Basic Drugs on Silica Columns Using Non-Aqueous Ionic Eluents. II. Application of UV, Fluorescence and Electrochemical Oxidation detection", *J. Chromatogr.*, 323(2): abstract only, 1985.

Bert, Maryse et al. "Non-Amphetaminic Central Stimulation by Alkaloids from the Ibogaine and Vobasine Series", *Planta Med.*, 54(3): abstract only, 1988.

Perera P. et al. "Tertiary Indole Alkaloids of Tabernaemontana Dichotoma Seeds", *Planta Med.*, 49/1: abstract only, 1983.

Shen- Ke-Fei and Crain, Stanley M. "Antagonists at Excitatory Opioid Receptors on Sensory Neurons in Culture Increase Potency and Specificity of Opiate Analgesics and Attenuate Development of Tolerance / Dependence", *Brain Research*, 636(2): abstract only, 1994.

Sershen, Henry et al. "Ibogaine Reduces Preference for Cocaine Consumption in C57BL/6By Mice", *Pharmacol., Biochem. Behav.*, 47(1): abstract only, 1994.

O'Hearn, E. and Molliver, M. E. "Degenration of Prukinje Cells in Parasagittal Zones of the Cerebellar Vermis After Treatment with Ibogaine of Harmaline", *Neuroscience*, 55(2): abstract only, 1993.

Keller, F. et al. "Modulation of Neopterin Release by Human Kupffer Cells in Culture: Possible Implication in Clinical Monitoring of HIV-Seropositive Subjects", *Cells Hepatic Sinusoid*, 3: abstract only, 1991.

Eberwine, J. H. and Mackler, S. A. "Molecular Analysis of Cellular Responses to Opiate Use", *Fidia Res. Found. Symp. Ser.*, 7(Neurotransm. Regul. Gene Transcr.): abstract only, 1991.

Lerida, M. et al. "Incidence of Morphine Withdrawal and Quasi-Abstinence Syndrome in a Model of Chronic Pain in the Rat", *Neurosci.*, 81(1-2): abstract only, 1987.

Shook, J. E. et al. "A cyclic Somatostatin Analog that Precipitates Withdrawal in Morphine-Dependent Mice", *NIDA Res. Monogr.*, 76(Probl. Drug Depend.): abstract only, 1987.

Palyi, Istvan. "Survivial Responses to New Cytostatic Hexitols of P388 Mouse and K562 Leukemia Cells in Vitro", *Cancer Treat. Rep.*, 70(2): abstract only, 1986.

Brady, Linda S. and Holtzman, Stephen G. "Analgesic Effects of Intraventricular Morphine and Enkephalins in Nondependent and Morphine-Dependent Rats", *J. Pharmacol. Exp. Ther.*, 222(1): abstract only, 1982.

Jaffe, Jerome H. "Psychopharmacology and Opiate Dependence", *U.S. Public Health Serv. Publ.*, 1957-1967:1836, 1967.

Widler, P. et al. "Pharmacodynamics and Pharmacokinetics of Khat: a Controlled Study", *Clin. Pharmacol. Ther.*, 55/5: abstract only, 1994.

Sheppard, S. G. "A Preliminary Investigation of Ibogaine: Case Reports and Recommendations for Further Study", *J. Subst. Abuse Treat.*, 11/4: abstract only, 1994.

Schnider, P. "Use and Abuse of Analgesics in Tension-Type Headache", *Cephalalgia*, 14/2: abstract only, 1994.

Keefner, S. M. "A Gas Chromatography-Mass Spectrometry (GCMS) Method for Ibogaine", *Society for Neuroscience Abstracts*, 19(1-3): abstract only, 1993.

Pantazis, P. et al. "Efficacy of Camptothecin Congeners in the Treatment of Human Breast Carcinoma Xenografts", *Oncology Research*, 5(8): abstract only, 1994.

O'Hearn, E. et al. "Ibogaine Induces Glial Activation in Parasagittal Zones of the Cerebellum", *Neuroreport*, 4/3: abstract only, 1993.

Nooter, K. and Sonneveld, P. "Multidrug Resistance (MDR) Genes in Haematological Malignancies", *Cytotechnology*, 12(1-3): abstract only, 1993.

Leoni, L. M. and Losa, G. A. "Effect of Cocaine and Morphine on Neutral Endopeptidase Activity of Human Peripheral Blood Mononuclear Cells Cultures with Lectins", *Cell Biochem Funct*, 11(3): abstract only, 1993.

Matharu, R. P. et al. "Preformulation and Development of Ibogaine Injection for the Treatment of Drug Abuse", *Pharmaceutical Research (New York)*, 10: abstract only, 1993.

Ma, J. Y. C. et al. "Inhibition of Respiratory Burst Activity in Alveolar Macrophages by Bisbenzylisoquinoline Alkaloids: Characterization of Drug-Cell Interaction", *Exp. Lung Res.*, 18/6: abstract only, 1992.

Glick, S. D. et al. "Effect of Ibogaine on Acute Signs of Morphine Withdrawal in Rats: Independence from Tremor", *Neuropharmacology*, 31/5: abstract only, 1992.

Qiu, B. S. et al. "The Influence of Chronic Nicotine Treatment on Stress-Induces Gastric Ulceration and Emptying Rate in Rats", *Experientia*, 48(4): abstract only, 1992.

Frances, B. et al. "Effects of Ibogaine on Naloxone-Precipitated Withdrawal in Morphine-Dependent Mice", *Fundam Clin Pharmacol*, 6(8-9): abstract only, 1992.

Pacifici, R. et al. "Immunological Effect of Cocaine and Host Resistance in Mice", *Int J Immunother*, 8(2): abstract only, 1992.

Halidas, J. A. et al. "Treatment of Crack Cocaine Use with Carbamazepine", *Am J Drug Alcohol Abuse*, 18(1): abstract only, 1992.

Villalba, Bedoya D. et al. "Uses and Abuses of Ipecacuana Syrup", *Farm. Clin.*, 9/1: abstract only, 1992.

Cankat, Tulunay F. "Pharmacological Aspects of Drug Induced Headache", *Funct. Neurol.*, 7/6: abstract only, 1992.

Haber, H. and Melzig, M. "Tetrahydroisoquinolines—Endogenous Products After Chronic Alcohol Abuse", *Pharmazie*, 47/1: abstract only, 1992.

Elkind, A. H. "Drug Abuse and Headache", *Med Clin North Am*, 75(3): abstract only, 1991.

Licht, T. Induction of Multiple-Drug Resistance During Anti-Neoplastic Chemotherapy In-Vitro, *Int J Cancer*, 49(4): abstract only, 1991.

Wishart, G. C. and Kaye, S. B. "Is Multidrug Resistance Relevant in Breast Cancer", *Eur. J. Surg. Oncol.*, 17/5: abstract only, 1991.

Fairchild, C. R. et al. "Keynote Address: Multidrug Resistance: A Pleiotropic Response to Cytotoxic Drugs", *Int. J. Radiat. Oncol. Biol. Phys.*, 20/2: abstract only, 1991.

Mizuhashi, F. et al. "Antitumor Activities of IKP-104 A 4-1H Pyridizinone Derivative on Cultured and Implanted Tumors", *Jpn J Cancer Res*, 81(12): abstract only, 1990.

Pehek, E. "Effects of Cathinone and Amphetamine on the Neurochemistry of Dopamine in Vivo", *Neuropharmacology*, 29/12: abstract only, 1990.

Kalix, P. "Pharmacological Properties of the Stimulant Khat", *Pharmacol. Ther.*, 48/3: abstract only, 1990.

Tsuruo, T. "Multidrug Resistance: A Transport System of Antitumor Agents and Xenobiotics", *Princess Takamatsu Symp*, 21: abstract only, 1990.

Nunn-Thompson, CL and Simon PA. "Pharmacotherapy for Making Cessation", *Clin Pharm*, 8(10): abstract only, 1989.

Wildmann, J. "Heterocycles as Physiological Ligands for the Benzodiazepine Receptor and for Other Binding Sites", *Pharmacol Res*, 21(6): abstract only, 1989.

Uldry PA and Regli, F. "Cerebrovascular Accidents in Relation to Drug Consumption or Drug Abuse", *Schweiz Rundsch Med Prax*, 78(23): abstract only, 1989.

Benoist, H. et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", *Cancer Immunol Immunother*, 30(5): abstract only, 1989.

Samadi-Baboli, M. et al. "Preparation of Low Density Lipoprotein-9-Methoxy-Illipticin Complex and Its Cytotoxic Effect Against L1210 and P 388 Leukemic Cells in Vitro", *Eur J Cancer Clin Oncol*, 25(2): abstract only, 1989.

Montefiori, DC et al. "In Vitro Evaluation of Mismatched Double-Stranded RNA (Ampligen) for Combination Therapy in the Treatment of Acquired Immunodeficiency Syndrome", *AIDS Res Hum Retroviruses*, 5(2): abstract only, 1989.

Tarnower, A. and Alguire, P. "Ergotism Masquerading as Arteritis", *Postgrad Med*, 85(1): abstract only, 1989.

Diener, H. C. et al. "Analgesic-Induced Chronic Headache Long-Term Results of Withdrawal Therapy", *J Neurol*, 236(1): abstract only, 1989.

Lemontt, J. F. et al. "Increase MDR Gene Expression and Decreased Drug Accumulation in Multidrug-Resistant Human Melanoma Cells", *Cancer Res*, 48(22): abstract only, 1988.

Sehested, M. et al. "The Carboxylic Ionophore Monensin Inhibits Active Drug Efflux and Modulates In-Vitro Resistance in Daunorubicin Resistant Enrlich Ascites Tumor Cells", *Biochem Pharmacol*, 37(17): abstract only, 1988.

Kalix, P. "Khat: A Plant with Amphetamine Effects", *J Subst Abuse Treat*, 5(3): abstract only, 1988.

Jansen, K. L. and Prast, C. J. "Ethnopharmacology of Kratom and the Mitragyna Alkaloids", *J Ethnopharmacol*, 23(1): abstract only, 1988.

Bussel, J. B. and Haimi, J. S. "Isolated Thrombocytopenia in Patients Infected with HIV Treatment with Intravenous Gamma Globulin", *Am J Hematol*, 28(2): abstract only, 1988.

Sugiyama, Y. et al. "Quantitative Analysis of Cell-Kill Effects of Anticancer Drugs: Consideration of Both In Vitro and In Vivo Expreimental Systems", *Gan To Kagaku Ryoho*, 14(12): abstract only, 1987.

Faglia, G. et al. "Dihydroergocryptine in Management of Microprolactinomas", *J Clin Endocrinol Metab*, 65(4): abstract only, 1987.

Hubens, G. et al. "Chronic Intake of a Hydrogenated Ergot Alkaloid Causing Peripheral Vascular Ischemia—A Case Report", *Vasc. Surg.*, 21/4: abstract only, 1987.

Metelitsa, V. I. "Pharmacological Agents in Controlling Smoking", *Biull Vsesoiuznogo Kardiol Nauchn Tsentra*, 10(1): abstract only, 1987.

Dierckx, R. A. et al. "Intraarterial Sodium Nitroprusside Infusion in the Treatment of Severe Ergotism", *Clin. Neuropharmacol.*, 9/6: abstract only, 1986.

Lewis, R. V. and McDevitt, D. G. "Adverse Reactions and Interactions with .beta.-Adrenoceptor Blocking Drugs", *Med. Toxicol.*, 1/5: abstract only, 1986.

Damstrup, L. and Jensen, T. T. "Retroperitoneal Fibrosis After Long-Term Daily Use of Ergotamine", *Int. Urol. Nephrol.*, 18/3: abstract only, 1986.

Saper, J. R. and Jones, J. M. "Ergotamine Tartrate Dependency: Features and Possible Mechanisms", *Clin. Neuropharmacol.*, 9/3: abstract only, 1986.

Wells, K. E. et al. "Recognition and Treatment of Arterial Insufficiency from Cafergot", *J. Vasc. Surg.*, 4/1: abstract only, 1986.

Holzner, F. and Barolin, G. S. "The Neuroleptic Sleeping Course in Chronic Headache", *Therapiewoche*, 35/36: abstract only, 1985.

Koch, H. K. et al. "Drug-Induced Liver Injury in Liver Biopsies of the Years 1981 and 1983, their Prevalence and Type of Presentation", *Path. Res. Pract.*, 179: abstract only, 1985.

Castle, W. M. "Drugs and Fibrotic Reactions—Part I", *Adverse Drug React. Bull.*, 113: abstract only, 1985.

Perrin, V. L. "Clinical Pharmacokinetics of Ergotamine in Migraine and Cluster Headache", *Clin. Pharmacokin.*, 10/4: abstract only, 1985.

Mateer, J. E. et al. "Reversible Ipecac Myopathy", *Arch. Neurol.*, 42/2: abstract only, 1985.

Gothoni, P. "Harmine-, Lon-954- and 5-Hydroxytryptophan-Induced Tremors in Rats Withdrawn from Ethanol", *Acta Pharmacol Toxicol*, 57(1): abstract only, 1985.

Isler, H. "Treatment of Headache", *Schweiz. Med. Wochenschr.*, 114/35: abstract only, 1984.

Hoes, M. J. "Clinical Criteria for the Selection of Anxiolytics", *Tijdschr. Ther. Geneesm. Onderz.*, 9/9: abstract only, 1984.

Henry, P. Y. et al. "Reversible Cerebral Arteriopathy Associated with the Administration of Ergot Derivatives", *Cephalalgia*, 4/3: abstract only, 1984.

Huang, C. C. et al. "Cytotoxicity and Sister Chromatid Exchanges Induced in Vitro by Six Anticancer Drugs Developed in the People's Republic of China", *J Natl Cancer Inst*, 71(4): abstract only, 1983.

Vescovi, P. P. et al. "Successful Treatment of Opiate Withdrawal Using Lysine Acetylsalicylate", *Curr. Ther. Res., Clin. Exp.*, 33/5: abstract only, 1983.

Beck, W. T. et al. "Energy-Dependent Reduced Drug Binding as a Mechanism of Vinca Alkaloid Resistance in Human Leukemic Lymphoblasts", *Mol Pharmacol*, 24(3): abstract only, 1983.

Williams, R. C. Jr. et al. "The 'Alice in Wonderland' Experience Ergot Alkaloid Therapy for Prolactin-Secreting Pituitary Tumors", *West. J. Med.*, 138/3: abstract only, 1983.

Worz, R. "Effects and Risks of Psychotropic and Analgesic Combinations", *Am. J. Med.*, 75/5A: abstract only, 1983.

Janzen, J. M. "History of Use of Psychotropic Drugs in Central Africa", *Psychotropes*, 1/2: abstract only, 1983.

Seeber. S. et al. "In Vivo Resistance Towards Anthracyclines, Etoposide, and Cis-Diamminedichloroplatinum (II)", *Cancer Res.*, 42(11): abstract only, 1982.

Menzies, K. E. and Isbister, W. H. "Gangrene of the Small Bowel: A Complication of Methysergide Therapy", *Aust. N. Z. J. Surg.*, 52/5: abstract only, 1982.

Ala, Hurula V. et al. "Erogotamine Abuse: Results of Ergotamine Discontinuation, with Special Reference to the Plasma Concentrations", *Cephalalgia*, 2/4: abstract only, 1982.

Tfelt-Hansen, P. et al. "Nitroglycerin for Ergotism. Experimental Studies in Vitro and in Migraine Patients and Treatment of an Overt Case", *Eur. J. Clin. Pharmacol.*, 22/2: abstract only, 1982.

Low, R. S. and Auersperg, N. "Effects of Acronycine and Cytouchalasin B on the Division of Rat Leukemia Cells", *Exp Cell Res*, 131(1): abstract only, 1981.

Criel, A. M. et al. "Drug Dependent Red Cell Antibodies and Intravascular Haemolysis Occurring in Patients Treated with 9 Hydroxy-Methyl-Ellipticinium", *Br J Haematol*, 46(4): abstract only, 1980.

Gold, M. S. et al. "Effect of Methadone Dosage on Clonidine Detoxification Efficacy", *Am. J. Psychiatry*, 137/3: abstract only, 1980.

Almeida, V. M. "Use and Abuse of Alcohol and Drugs a Clinical Study of Certain Aspects of Their Interrelationship", *Bol of Sanit Panam*, 88(1), 1980.

Gross, R. J. "Effect of Ergot Alkaloids on Serum Prolactin in Non-Psychotic Organic Brain Syndrome of the Elderly", *Exp Aging Res*, 5(4): abstract only, 1979.

Knoll, J. "Azidomorphines: A New Family of Potent Analgesics with Low Dependence Capacity", *Prog. Neuro-Psychopharmacol.*, 3/1-3: abstract only, 1979.

Heel, R. C. et al. "Buprenorphine: A Review of Its Pharmacological Properties and Therapeutic Efficacy", *Drugs*, 17(2): abstract only, 1979.

Konig, P. "Psychiatric Intensive Therapy After Acute Alkaloid Withdrawal Syndrome", *Infusionsther Klin Ernahr*, 6(1): abstract only, 1979.

Finkle, H. I. "Phencyclidine Identification by Thin-Layer Chromatography. A Rapid Screening Procedure for Emergency Toxicology", *Am. J. Clin. Pathol.*, 70/2: abstract only, 1978.

Blum, K. et al. "Putative Role of Isoquinoline Alkaloids in Alcoholism: A Link to Opiates", *Alcohol Clin Exp Res*, 2(2): abstract only, 1978.

Whittaker, J. A. and Griffith, I. P. "Recurrent Laryngeal Nerve Paralysis in Patients Receiving Vincristine and Vinblastine", *Br Med J*, 1(6071): abstract only, 1977.

Blum, K. et al. "Peyote a Potential Ethnopharmacologic Agent for Alcoholism and Other Drug Dependencies Possible Biochemical Rationale", *Clin Toxicol*, 11(4): abstract only, 1977.

Azevedo, I. and Osswald, W. "Adrenergic Nerve Degeneration Induced by Condensation Products of Adrenaline and Acetaldehyde", *Naunyn-Schmiedeberg's Arch Pharmacol*, 300(2): abstract only, 1977.

Melchior, C. L. and Myers, R. D. "Preference for Alcohol Evoked by Tetra Hydro Papaveroline Chronically Infused in the Cerebral Ventricle of the Rat", *Pharmacol Biochem Behav*, 7(1): abstract only, 1977.

Knoll, J. "Azidomorphines and Homopyrimidazols: A New Approach to the Ideal Analgetic", *Acta Physicol Pharmacol Bulg*, 3(2): abstract only, 1977.

Alexander, G. J. "A Procedure for Drug Screening Without the Need to Transport Urines Use of Ion Exchange Papers and Hem Agglutination Inhibition", *Clin Toxicol*, 9(3): abstract only, 1976.

Blum, K. et al. "Possible Role of Tetrahydroisoquinoline Alkaloids in Postalcohol Intoxication States", *Ann N Y Acad Sci*, 273: abstract only, 1976.

Evenson, M. A. "Developments in Therapeutic Drug Monitoring and Alkaloid Analysis", *Fed Proc*, 34(12): abstract only, 1975.

Smith, A. A. "Interaction of Biogenic Amines with Ethanol", *Adv Exp Med Biol*, 56: abstract only, 1975.

Gabr, A. I. et al. "Changes in Absolute Amount of Alkaloids in Datura-Metel Treated with Certain Growth Regulators", *Herba Pol*, 21(2): abstract only, 1975.

Beaubrun, M. H. "The Diagnosis and Management of Acute Psychotic Reaction Due to Alcohol and Drugs", *Caribb Med J*, 36(1): abstract only, 1975.

Caldwell, J. and Sever, P. S. "The Biochemical Pharmacology of Abused Drugs. III. Cannabis, Opiates, and Synthetic Narcotics", *Clin. Pharmacol. Ther.*, 16/6: abstract only, 1974.

Lewis, J. W. et al. "Narcotic Analgesics and Antagonists", *Annu Rev Pharmacol*, 11: abstract only, 1971.

Ban, T. A. "Adverse Effects to Psychotomimetics. Proposition of a Psychopharmacological Classification", *Radouco-Thomas S, ed. Pharmacologie, Toxicologie, et abus des l'Universite Laval*, QV 109: abstract only, 1974.

Chemical abstract, RN 481-87-8 Registry.

Chemical abstract, RN 88660-09-7 Registry.

Chemical abstract, RN 88660-07-5 Registry.

Chemical abstract, RN 77123-15-0 Registry.
Chemical abstract, RN 57511-56-5 Registry.
Chemical abstract, RN 53508-36-4 Registry.
Chemical abstract, RN 16671-16-2 Registry.
Chemical abstract, RN 4865-78-5 Registry.
Chemical abstract, RN 3464-63-9 Registry.
Krug, S. E. "Cocaine Abuse: Historical, Epidemiologic, and Clinical Perspectives for Pediatricians", *Advances in Pediatrics*, 36: abstract only, 1989.
Al-Shabanah, O. A. et al. "Gastric Antiulcer and Cytoprotective Effects of Cathinone, a Psychoactive Alkaloid of Khat (Catha Edulis Forsk.) And Amphetamine in Rats", *Regulatory Peptides*, abstract only, 1994.
Alim, T. N. et al. "Open-Label, Dose Run-Up Study of Diethylpropion in Initial Cocaine Abstinence", *Clinical Neuropharmacology*, 17(2): abstract only, 1994.
Pulvirenti, L. and Koob, G. F. "Lisuride Reduces Intravenous Cocaine Self-Administration in Rats", *Pharmacology, Biochemistry and Behavior*, 47(4): abstract only, 1994.
McNeish, C. S. et al. "The 5-HT Sub 3 Antagonist Zacopride Attenuates Cocaine-Induced Increases in Extracellular Dopamine in Rat Nucleus Accumbens", *Pharmacology, Biochemistry, and Behavior*, 45(4): abstract only, 1993.
Mattingly, B. A. et al. "Selective Antagonism of Dopamine D Sub1 and D Sub 2 Receptors Does Not Block the Development of Behavioral Sensitization to Cocaine", *Psychopharmacologia*, 114(2): abstract only, 1994.
Siew, Koon Teoh et al. "Buprenorphine Effects on Morphine- and Cocaine- Induced Subjective Responses by Drug—Dependent Men", *Journal of Clinical Psychopharmacology*, 14(1): abstract only, 1994.
Martellotta, M. C. et al. "Effects of the Calcium Antagonist Isradipine on Cocaine Intravenous Self-Administration in Rats", *Psychopharmacologia*, 113(3-4): 1994.

Valadez, A. and Schenk, S. "Persistence of the Ability of Amphetamine Preexposure to Facilitate Acquistion of Cocaine Self-Administration", *Pharmacology, Biochemistry and Behavior*, 47(1): abstract only, 1994.
Rodriguez, W. A. et al. "Cocaine Adminstration Prior to Reactivation Facilitates Later Acquisition of an Avoidance Response in Rats", *Psychopharmacologia*, 112(2-3): abstract only, 1993.
Ricceri, L. et al. "Postnatal cocaine Esposure Affects Neonatal Passive Avoidance Performance and Cholinergic Development in Rats", *Pharmacology, Biochemistry and Behavior*, 45(2): abstract only, 1993.
Nishiyama, K. et al. "Expression of the Multidrug Transporter, P-Glycoproteiin, in Renal and Transitional Cell Carcinomas", *Cancer*, 71(11): abstract only, 1993.
Sachs, R. et al. "Corneal Complications Associated with the Use of Crack Cocaine", *Ophthalmology*, 100(2): abstract only, 1993.
Gifford, A. N. and Johnson, K. M. "Effect of Chronic Cocaine Treatment on D SUB 2 Receptors Regulating the Release of Dopamine and Acetylcholine in the Nucleus Accumbens and Striatum", *Pharmacology, Biochemistry and Behavior*, 41(4): abstract only, 1992.
Ala-Hurula, V. et al. "Tolfenamic Acid and Ergotamine Abuse", *Headache*, 21(6): abstract only, 1981.
Chemical abstract, RN 83-74-9 Registry.
Popik, P., et al. Pharmacological Reviews 47 (2) 1995, pp. 235-253.
Bahargava et al., Brain Research (1997) 752:234-238.
Glick et al., Brain Research (1996) 713:294-297.

* cited by examiner

NORIBOGAINE IN THE TREATMENT OF PAIN AND DRUG ADDICTION

RELATED APPLICATIONS

The present application is a §371 of PCT/US98/18284, filed 3 Sep. 1998, which claims priority from provisional application Ser. No. 60/057,921, filed 4 Sep. 1997.

FIELD OF THE INVENTION

The present invention is concerned with novel pharmaceutical compositions and novel treatment methods. In particular, the invention relates to novel methods for providing analgesia and to novel pharmaceutical compositions containing the drug noribogaine. The compositions particularly include those containing, in addition to noribogaine, one or more opioid antagonists. In addition, the present invention provides novel compositions and methods useful in treating patients for the symptoms associated with withdrawal from drug dependency or abuse.

BACKGROUND OF THE INVENTION

Ibogaine is an indole alkaloid derived from *Tabernanth iboga*, a shrub of West Africa, and is used by indigenous people of that region in religious rituals. The structure of ibogaine has been determined and procedures for its synthesis have been reported (see, Buchi, et al., *J. Am. Chem. Soc.* 88:3099 (1966); Rosenmund, et al., *Chem. Ber.* 108: 1871 (1975); and Huffman, et al., *J. Org. Chem.* 50:1460 (1985)). The chemical structure is as follows:

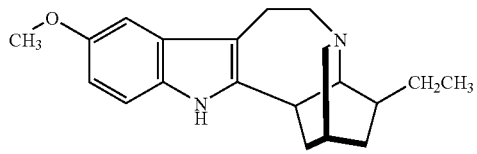

In 1956 Salmoiraghi and Page elucidated ibogaine's relationship to serotonin (*J. Pharm. and Exp. Ther.* 120(1): 20–25 (1957)). About the same time Schneider published three important papers: "Potentiation Action of Ibogaine on Morphine Analgesia" (*Experiential* 12:323–24 (1956)); "Neuropharmacological Studies of Ibogaine: An Indole Alkaloid with Central Stimulant Properties," (*Ann. of N.Y. Acad. Sci.* 66:765–76 (1957)); and "An Analysis of the Cardiovascular Action of Ibogaine HCl," (*Arch. Int. Pharmacodyn.* 110:92–102 (1957)). Dhahir published a review of the pharmacology and toxicology of ibogaine in his doctoral thesis, "A Comparative Study of the Toxicity of Ibogaine and Serotonin" (University Microfilms International 71-25-341, Ann Arbor, Mich.). The thesis gives an overview of much of the work accomplished with ibogaine.

Additional studies of interest include: "The Effects of Some Hallucinogens on Aggressiveness of Mice and Rats" (Kostowski, et al., *Pharmacology* 7:259–63 (1972)), "Cerebral Pharmacokinetics of Tremor-Producing Harmala and Iboga Alkaloids" (Zetler, et al., *Pharmacology* 7(4):237–248 (1972)), "High Affinity $^3$H-Serotonin Binding to Caudate: Inhibition by Hallucinogenic and Serotonergic Drugs" (Whitaker, et al., *Psychopharmacology* 59:1–5 (1978)); "Selective Labeling Of Serotonin Receptors by d-($^3$H)Lysergic Acid Diethylamide in Calf Caudate" (*Proc. Natl. Acad. Sci., U.S.A.* 75(12):5783–87 (1978)); and "A Common Mechanism of Lysergic Acid, Indolealkylamine and Phenethylamine Hallucinogens: Serotonergic Mediation of Behavioral Effects in Rats" (Sloviter, et al., *J. Pharm. Exp. Ther.* 214(2):231–38 (1980)). More current work has been reported by Dzoljic, et al., "Effect of Ibogaine on Naloxone-Precipitated Withdrawal Syndrome in Chronic Morphine Dependent Rats," (*Arch. Int. Pharmacodyn.*, 294:64–70 (1988)).

Ibogaine administration has been reported to reduce the withdrawal symptoms associated with drug dependency and to alleviate drug cravings in addicts. It has been disclosed to be effective in the treatment of dependencies resulting from a wide range of drugs, including narcotics (U.S. Pat. No. 4,499,096); cocaine and amphetamines (U.S. Pat. No. 4,587,243); alcohol (U.S. Pat. No. 4,857,523); and nicotine/tobacco (U.S. Pat. No. 5,026,697). In addition it has been reported to be effective in patients addicted to multiple drugs and drug combinations (U.S. Pat. No. 5,152,994). Among the specific drug dependencies reportedly amenable to ibogaine treatment are heroin, cocaine, alcohol, nicotine, caffeine, amphetamine, desoxyephedrine, methadone and combinations thereof.

Other pharmacological agents that have been used in the treatment of certain types of drug addiction or dependency include naloxone and naltrexone. However, these agents typically fail to alleviate the often severe suffering that accompanies the drug withdrawal process and are generally ineffective in treating polydrug abuse or addiction. Thus, the prior art has failed to provide a completely satisfactory therapy for drug addiction or abuse and new agents and methods are clearly needed.

SUMMARY OF THE INVENTION

In accordance with the present invention, surprising and unexpected properties of noribogaine have been discovered. This compound is known to be a metabolite of ibogaine and is chemically identified as 12-hydroxyibogamine. In particular, noribogaine has been found to be useful as a non-addictive analgesic agent and as a treatment for drug dependency or abuse. Pharmaceutical compositions of noribogaine can be combined with one or more known opioid antagonists to treat addiction such that withdrawal symptoms are substantially eliminated or, at a minimum, surprisingly reduced. Such compositions are conveniently prepared in unit dose form with one or more unit doses providing a therapeutically effective amount of active ingredient.

In its first aspect, the invention is directed to a method of alleviating pain in a patient by administering systemically noribogaine at a therapeutically effective dosage. In a preferred embodiment, administration is by means of a pharmaceutical composition in which noribogaine is the sole analgesic agent. In patients for whom opioid analgesics are contraindicated, noribogaine is administered systemically in an amount of effective to reduce or eliminate pain in the absence of any concomitant opioid analgesic therapy. In each case, the dosage of noribogaine administered to a patient should be between 0.1 and 100 mg per kg of body weight and, preferably, between 1 and 30 mg per kg of body weight.

The present invention also includes a method of treating a patient to alleviate pain by administering systemically noribogaine and one or more opioid antagonists, such that the respective amounts of noribogaine and antagonist are effective to reduce or eliminate pain. If desired, one or more opioid antagonists may also be administered to patients, with the preferred antagonist being naloxone, naltrexone or nalorphine, preferably at a concentration of between 0.15 mg and 0.5 mg for each mg of noribogaine administered. Although, the method is compatible with any route of administration, the transdermal route will generally be the most convenient.

The invention is also directed to a method for treating drug addiction (involving drug dependency or drug abuse) during withdrawal therapy by administering noribogaine to a patient at a dosage sufficient to reduce or eliminate one or more symptoms associated with withdrawal. Such symptoms include nausea, vomiting, anxiety, abdominal cramps, muscle pain, chills and headache. In addition, noribogaine treatment decreases the drug cravings normally experienced by addicts after cessation of the self administration of the abused substance. Noribogaine is especially useful in the treatment of addiction to narcotics such as heroin and methadone. However, it is also useful in treating patients addicted to cocaine, alcohol, amphetamines and combinations of these drugs. It is preferred that the noribogaine be administered to patients suffering from drug dependence or abuse in conjunction with an opioid antagonist such as naloxone, naltrexone or nalorphine. The dosage of noribogaine should be as discussed above in conjunction with its use in the alleviation of pain. Again, the transdermal route of administration is generally preferred.

In addition to the methods discussed above, the present invention is directed to a pharmaceutical composition, preferably in unit dose form, comprising noribogaine and one or more opioid antagonists. When administered to a patient, one or more unit doses provide an amount of noribogaine and of opioid antagonist effective to treat drug dependency or to provide analgesia. Noribogaine should generally be present in such compositions at a concentration of between about 0.1 and 20 mg/ml. When either naloxone or naltrexone is used as an opioid antagonist in compositions, they should be present at 0.05 to 0.5 mg for each mg of noribogaine.

The present invention contemplates that the administration of active ingredients will be accomplished by any systemic route which is convenient and readily accessible to the attending physician. While all of the various conventional routes of administration are contemplated (e.g., transdermal, intranasal, intramuscular, subcutaneous, intravenous, vaginal, rectal, buccal and oral), the preferred route of administration is transdermally.

The present invention further contemplates the use of noribogaine as an adjunct to conventional drug withdrawal therapy, specifically providing for the administration of noribogaine concomitantly with one or more opioid antagonists. "Concomitant" administration refers to the administration of the two agents (i.e., noribogaine and an opioid antagonist) in any manner in which the pharmacological effects of both are manifest in the patient at the same time. Thus, concomitant administration does not require that a single pharmaceutical composition, the same dosage form, or even the same route of administration be used for administration of both noribogaine and opioid antagonist or that the two agents be administered at precisely the same time. However, concomitant administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

Pharmaceutical compositions in accordance with the invention are prepared by conventional means using methods known in the art. For example, there are known in the art methods for the preparation of opioid antagonist pharmaceutical compositions fully adaptable to the preparation of compositions of both noribogaine and opioid antagonists. Solid pharmaceutical compositions are provided in accordance with the present invention in unit dosage form. A unit dosage for a solid pharmaceutical composition refers to the amount of each of the active ingredients which is administered in any one entity. Thus, the unit dosage form of a solid pharmaceutical composition makes reference to a discreet entity (e.g., a capsule, tablet, suppository, or drug-releasing device), one or more of which entities contains an appropriate dosage for a single administration.

Accordingly, solid pharmaceutical compositions in accordance with the invention are adaptable to provide administration by transdermal, intranasal, oral, vaginal, rectal, and buccal routes. However, for parenteral routes (e.g., subcutaneous, intravenous, and intraarterial) novel liquid pharmaceutical compositions in accordance with the present invention are provided. Also provided are novel liquid pharmaceutical compositions suitable for oral administration (e.g., syrups and elixirs). Each of these pharmaceutical compositions is prepared by methods known in the art.

DETAILED DESCRIPTION OF THE INVENTION

Figure 1A:
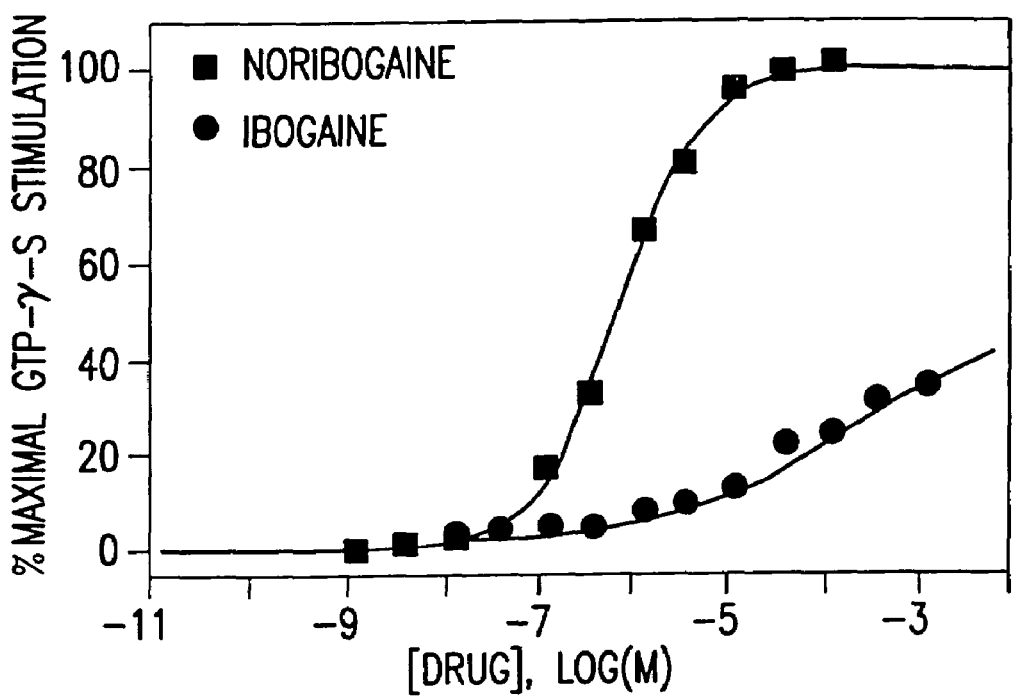
FIG. 1 (panels A and B): Panel A shows the stimulation of [$^{35}$S]GTPγS binding to rat thalamic membranes by various concentrations of noribogaine (■) and ibogaine (●). Results are expressed as percent maximal stimulation (defined by 10 μM DAMGO). Panel B shows the inhibitory shift of noribogaine-stimulated [$^{35}$S]GTPγS binding by naloxone (0.1 μM).

Noribogaine, a metabolite of ibogaine, has properties that are well suited to the treatment of pain and to the withdrawal symptoms associated with drug dependency or abuse. In particular, it has been discovered that noribogaine binds to two classes of opioid receptors that have been associated with pain relief, the μ and κ receptors. In the case of the μ-type receptors, it appears that noribogaine acts as a full opiate agonist. In addition, noribogaine elevates brain serotonin levels by blocking synaptic reuptake. It is believed that such levels (as well as ligand interactions at the μ and κ opiate receptors) play a role in the anxiety and drug cravings experienced by addicts during withdrawal.

Noribogaine is synthesized by the O-demethylation of ibogaine. This may be accomplished, for example, by reacting ibogaine with boron tribromide/methylene chloride at room temperature and then purifying the product using known procedures. At present, noribogaine may also be obtained from the National Institute on Drug Abuse (Rockville, Md.). The compound has the following structure:

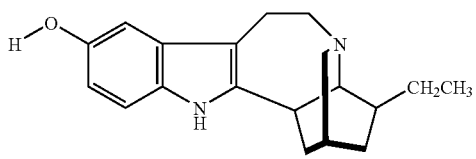

Chemical Form of Noribogaine

The present invention is not limited to any particular chemical form of noribogaine and the drug may be given to patients either as a free base or as a pharmaceutically acceptable acid addition salt. In the latter case, the hydrochloride salt is generally preferred, but other salts derived from organic or inorganic acids may also be used. Examples of such acids include, without limitation, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like. As discussed above, noribogaine itself may be formed by the O-demethylation of ibogaine which, in turn, may be synthesized by methods known in the art (see e.g., Huffman, et al., *J. Org. Chem.* 50:1460 (1985)).

Preferred Dosage Forms and Route of Administration

As noted above, any route of administration and dosage form is compatible with the treatments discussed above and noribogaine may be administered as either the sole active agent or in combination with other therapeutically active drugs. In this regard, it is preferred that pharmaceutical compositions, especially those used in the treatment of drug addiction or abuse, contain one or more opioid antagonists. Although compositions suitable for oral delivery will probably be used most frequently, other routes that may be used include peroral, internal, pulmonary, rectal, nasal, vaginal, lingual, intravenous, intraarterial, intramuscular, intraperitoneal, intracutaneous and subcutaneous routes. Especially preferred is the transdermal route of delivery in which drug is applied as part of a cream, gel or, preferably, patch (for examples of transdermal formulations, see U.S. Pat. Nos. 4,806,341; 5,149,538; and 4,626,539). Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., *Remington's Pharmaceutical Sciences*, 16th ed., A. Oslo editor, Easton Pa. 1980)).

Noribogaine is preferably used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

When formulating compositions containing noribogaine in combination with an opioid antagonist, the preferred antagonist will be naloxone, naltrexone or nalorphine. These agents are commercially available and have been approved for the treatment of opioid withdrawal. In general, noribogaine or a pharmaceutically acceptable salt of noribogaine should be present in the pharmaceutical compositions at a concentration of between 0.1 and 20 mg/ml. Naloxone, naltrexone, or nalorphine should preferably be present at about 0.05 to about 0.5 mg for each mg of noribogaine. The antagonist may be added in any chemical form which is stable in the particular formulation being prepared.

Method of Treatment

Patients will be administered noribogaine or a composition containing noribogaine together with opioid antagonist, either for the treatment of pain or for the treatment of drug dependency or abuse. In either case, dosage will be selected to reduce or eliminate one or more of the symptoms experienced by the patient. Thus, when noribogaine is being administered as an analgesic, sufficient drug should be given to reduce or eliminate the patient's pain. In the case of drug withdrawal, noribogaine should be given at a dosage sufficient to reduce symptoms commonly associated this process, for example, headache and muscular pain, and preferably at a dosage sufficient to also reduce drug cravings. For both treatments, daily dosage will typically be between 0.1 mg and 100 mg of noribogaine per kg of patient body weight and preferably between 1 mg and 30 per kg of patient body weight. Dosage may be provided in single or divided doses. These dosages are simply guidelines and the actual dose selected for an individual patient will be determined by the attending physician based upon clinical conditions and using methods well known in the art. Compositions may be provided in either a single or multiple dosage regimen, (e.g., a patient may take 3 mg of a noribogaine composition orally three times a day). Alternatively, drug may be administered in an essentially continuous manner using a transdermal preparation or patch.

When noribogaine is used in the treatment of pain, administration may be required on a long term basis and the drug may be taken in a prescribed regimen (as discussed above) or as needed by the patient. Long term treatment may also be necessary in the treating patients for drug dependency or abuse. Sustained release dosage forms or transdermal patches are generally preferred in treating these patents.

Advantages

One of the main advantages of noribogaine is that it is not habit forming. Thus, pain relief can be accomplished without the risk of dependence associated with the chronic use of narcotics. Similarly, patients treated for drug dependence or abuse may be given noribogaine without the abuse/dependence problems presented by treatment with agents such as methadone. In fact, patients participating in drug substitution programs may want to use noribogaine to taper off the substitute. Also, by alleviating some of the worst aspects of the drug withdrawal process, noribogaine should be a form of therapy that people dependent upon, or abusing, drugs will find acceptable.

EXAMPLES

Figure 1B:
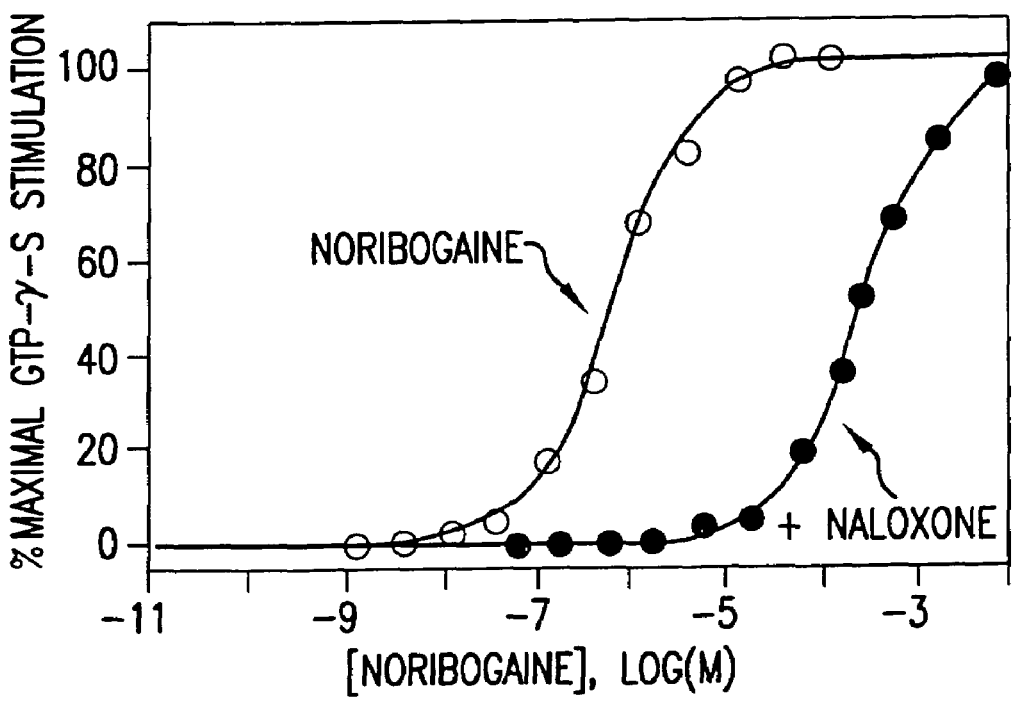

Noribogaine-stimulated [$^{35}$S]GTPγS binding to rat thalamic membranes was used to measure receptor activation of G proteins and results are shown in FIG. 1 and Table 1. The percent maximal stimulation (10 μM DAMGO, $EC_{50}$=7.4+/−0.1 nM) of [$^{35}$S]GTPγS binding stimulated by noribogaine was determined in the presence of an excess of GDP. The $EC_{50}$ value for noribogaine-stimulated binding was 0.324+/−0.015 μM. In contrast, ibogaine caused a weak stimulation of [$^{35}$S]GTPγS binding even at concentrations above 100 μM. Noribogaine-stimulated binding was blocked in the presence of naloxone (competitive antagonist, EC$_{50}$=35+/−1.8 μM), demonstrating further that the effect of noribogaine was μ-receptor mediated. The rightward shift of the concentration/effect relationship of noribogaine-stimulated binding with increasing concentration of naloxone was similar to that measured for DAMGO in the presence of competitive antagonist. The level of [$^{35}$S]GTPγS binding stimulated by noribogaine was in close agreement to the maximal number of [$^{35}$S]GTPγS binding sites that could be occupied after DAMGO stimulation of G proteins.

Taken together, these results demonstrate that noribogaine acts as a full agonist of the μ-opioid receptor and that it has efficacy as an antinociceptive agent that can used without the abuse liability inherent opiates. Results also indicate that noribogaine may effectively be used, either alone or in conjunction with an opioid antagonist, in the treatment of drug addition.

TABLE 1

Stimulation of [$^{35}$S]GTPγS Binding to Rat (Sprague Dawley) Thalamic Membranes by Opioid Agonists of Varying Efficacy

| Drug | [$^{35}$S]GTPγS Binding EC$_{50}$ (nM) |
| --- | --- |
| Buprenorphine | 0.7 ± 0.1 |
| DAMGO | 7.4 ± 0.1 |
| Morphine | 52 ± 6.3 |
| Noribogaine | 324 ± 15.5 |
| Naloxone | NE |
| Buprenorphine + Naloxone | 301 ± 44 |
| DAMGO + Naloxone | 2,230 ± 131 |
| Morphine + Naloxone | 26,000 ± 842 |
| Noribogaine + Naloxone | 236,000 ± 3,410 |

Values are means ± S.E. from three or more separate experiments. EC$_{50}$ = concentration of drug producing half maximal stimulation of binding.

All references cited herein are fully incorporated by reference. Having now fully described in the invention, it will be understood by those of skill and the art that the invention may be practiced within a wide and equivalent range of conditions, perimeters and the like without effecting the spirit or scope of the invention or any embodiments thereof.

What is claimed is:

1. A method of treating a patient to alleviate nociceptive pain in the absence of the treatment of drug dependence or drug abuse comprising: administering systemically to said patient a pharmaceutical composition consisting essentially of an effective amount of noribogaine or its pharmaceutically acceptable salt to said patient effective to reduce or eliminate said nociceptive pain in said patient, wherein the noribogaine or its salt is the sole analgesic agent administered.

2. The method of claim 1, wherein said noribogaine or its salt is administered to said patient at a dose of between 0.1 mg and 100 mg per kg of body weight.

3. The method of claim 2, wherein said noribogaine or its salt is administered at a dose of between 1.0 mg and 30 mg per kg of body weight.

4. A method of treating a patient to alleviate nociceptive pain in the absence of the treatment of drug dependency or drug abuse, comprising:
   a) administering systemically to said patient an amount of noribogaine or its pharmaceutically acceptable salt; and
   b) concomitantly administering systemically to said patient an amount of one or more opioid antagonists; wherein said respective amounts of noribogaine and said one or more opioid antagonists are effective to reduce or eliminate nociceptive pain in said patient, and wherein the noribogaine or its salt is the sole analgesic administered.

5. The method of claim 4, wherein said opioid antagonist is naloxone, administered to said patient at a dose between 0.05 mg and 0.5 mg for each mg of noribogaine.

6. The method of claim 4, wherein said opioid antagonist is naltrexone, administered to said patient at a dose of between 0.05 mg and 0.5 mg for each mg of noribogaine.

7. The method of claim 4, wherein said noribogaine and said opioid antagonist are administered transdermally.

8. The method of claim 4, wherein said noribogaine or its salt is administered to said patient at a dose of between 0.1 mg and 100 mg per kg of body weight.

9. The method of claim 8, wherein said noribogaine or its salt is administered at a dose of between 1.0 mg and 30 mg per kg of body weight.

* * * * *